United States Patent
Sahiri et al.

(10) Patent No.: US 7,483,138 B2
(45) Date of Patent: Jan. 27, 2009

(54) DEVICE FOR ANALYSIS OR ABSORPTION MEASUREMENT ON A SMALL AMOUNT OF LIQUID

(75) Inventors: Thomas Sahiri, Wehriestrasse 33, Munchen (DE) 81679; Holm Kandler, Auggen (DE)

(73) Assignees: Hellma GmbH & Co. KG, Mullheim (DE); Thomas Sahiri, Munich (DE)

( * ) Notice: Subject to any disclaimer, the term of this patent is extended or adjusted under 35 U.S.C. 154(b) by 0 days.

(21) Appl. No.: 11/995,332

(22) PCT Filed: Jul. 12, 2006

(86) PCT No.: PCT/EP2006/006808

§ 371 (c)(1), (2), (4) Date: Jan. 11, 2008

(87) PCT Pub. No.: WO2007/017035

PCT Pub. Date: Feb. 15, 2007

(65) Prior Publication Data

US 2008/0204755 A1    Aug. 28, 2008

(30) Foreign Application Priority Data

Aug. 5, 2005    (DE) .................. 10 2005 036 898

(51) Int. Cl.
*G01N 21/00* (2006.01)

(52) U.S. Cl. .................. 356/432; 356/246
(58) Field of Classification Search .................. 356/432, 356/246
See application file for complete search history.

(56) References Cited

U.S. PATENT DOCUMENTS 4,707,123 A    11/1987    McLachlan et al.

(Continued)

FOREIGN PATENT DOCUMENTS

DE    9403540.7    5/1994

(Continued)

OTHER PUBLICATIONS

Schiek, Oswald, Technische Optik, Zentralstelle fur Fachschulausbildung. 1961, pp. 80-85, Dresden.

*Primary Examiner*—Roy M Punnoose
(74) *Attorney, Agent, or Firm*—Volpe and Koenig, PC

(57) ABSTRACT

A device (1) for analysis of absorption measurement on small amounts, for example on a drop or droplet of a liquid medium (2) using light (3) is provided, with an upper planar location (4) for the application or dropping of the medium (2), a light entry (5) in the housing (6) arranged beneath the location surface or receiving position (4) and a first device (7) in the light beam behind the light entry (5) for deflection of the light upwards to the receiving position (4) where a detachably mounted reflector (8) is also located. The device (7) for deflecting the light beam is designed such that the direction of the optical axis of the deflected light beam is oriented upwards toward the middle (M) of the device (1) and the inclined position of the optical axis of the light beam with regard to the device mid-point (M) is arranged to be directed at the position of the reflector (8) through which the longitudinal median (M) between the light entry (5) and the light exit from the device (1) extends. The height of the assembly of the device (1) relative to such a device in which the light is first deflected about a right angle and only then after a further direction change is directed at the receiving position (4) or the sample, is correspondingly lower.

18 Claims, 2 Drawing Sheets

U.S. PATENT DOCUMENTS 5,185,834 A * 2/1993 Day et al. .................... 385/47
5,311,283 A   5/1994 Heeschen
2002/0024018 A1 2/2002 Saito et al.

FOREIGN PATENT DOCUMENTS

DE    102004023178    12/2005
EP        0660106      8/1994

* cited by examiner

DEVICE FOR ANALYSIS OR ABSORPTION MEASUREMENT ON A SMALL AMOUNT OF LIQUID

BACKGROUND

The invention relates to a device for the analysis or absorption measurement on a small amount, for example, on a droplet of a liquid medium with the help of light, which is guided through the medium and can then be detected or analyzed with a photometer, spectrophotometer, fluorometer, or spectrofluorometer, wherein the device has, in the position of use, an upper planar receiving location for the deposition or dropping of the medium, a light entry located, in the position of use, underneath the receiving location, in its housing, and a first device located in the beam path behind the light entry for deflecting the light upward to the receiving location and a reflector that can be mounted detachably above the receiving location and that has a defined distance from the receiving location in its position of use and is filled or can be filled by the medium at least in the area of the light passage, wherein a second device for deflecting the light coming from the reflector toward a detector is provided.

Such a device is described in the German Patent Application 10 2004 023 178.8 and has proven itself in practice. However, it has been shown that the provided light guidance, in which the optical axis of the light beam is deflected upward perpendicular to its direction provided at the entry to the device and then is guided to the actual measurement location, results in an overall height that is unfavorable for many applications.

SUMMARY

Therefore, there is the objective of providing a device of the type defined above, in which its advantages, placing small sample amounts of a liquid medium in a simple way onto a measurement location and being able to clean reliably and easily after the measurement, are maintained and, nevertheless, the overall height can be reduced.

To meet this objective, it is provided, for the device defined above, that the first device arranged at the light entry is constructed for deflecting the light beam, so that the resulting direction of the optical axis of the deflected light beam is oriented upwards and at an angle to the middle of the device and the inclined position of the optical axis is arranged relative to the device middle, so that the optical axis of the light beam or light beam bundle without or with the help of at least one optical element is directed toward the position of the reflector, through which the longitudinal middle extends between the light entry and the light exit of the device.

Through this angled position of the light beam bundle through its first deflection, a clearly lower overall height results than when the light beam bundle is first deflected by 90° and only then oriented toward the middle of the device and the reflector, because the distance of the reflector from the light entry can be smaller, in order, nevertheless, to be intersected by the light beam at the "light spot," namely at the receiving position for the sample. For this solution, the knowledge is required that for deflecting the light, a typical right-angle prism is not to be used for deflecting the light.

It is especially advantageous when the light beam reaches the reflector without an optical element, because then the expense for a corresponding optical element, for example, for an optical waveguide, can be spared.

However, it is also possible that at least one lens and/or one prism and/or one optical waveguide is provided as an optical element for the deflected light beam to the reflector and then from the reflector to the light exit or to a second device located at the light exit for deflecting the light beam. Such an arrangement has the advantage of better and more precise light guidance.

The already mentioned alternatives, according to which the light beam runs without guiding out from the deflection or redirected to the receiving position, can be used, first, if it has a correspondingly small divergence or convergence or runs at least through a convex lens.

It can be useful if an optical element is provided as a window and/or for bundling the light beam, for example, a convex lens, before and/or after the entry of the deflected light beam into the open space crossed by it or into an optical waveguide.

An especially advantageous construction of the invention can be provided in that the optical axis of the light beam extends before and/or at the light entry into the housing horizontally and that the first device for deflecting the light beam, whose optical axis is deflected upward by less than 90°, especially by approximately 80° to 89°, preferably by approximately 85°. Instead of the right-angle deflection, relative to the original direction of the optical axis, a smaller deflection is performed, so that the deflected beam from the deflection point is directed at an angle to this middle relative to the longitudinal middle of the housing of the device, in order to be directed practically directly to the position of the device for correct alignment of the deflection and also, if necessary, with the help of the already mentioned optical elements, where the sample is located and is to be transited by the light. Deflection first by a right angle and then another deflection in the direction to the sample with corresponding expense and resulting larger overall height is to be avoided.

A structurally simple construction of the invention can be provided in that, in the region of the light entry, as a first device for deflection, a deflection prism or a deflection mirror is provided, whose reflective surface has an angle less than 45° relative to the optical axis of the incident light beam. By changing the angular position of the reflective surface of the deflection prism or the deflection mirror from the typical 45° angular position, the deflection of the light beam deviating from a right angle according to the invention can be implemented very easily.

Here, on the prism, the surface, through which the light beam exits after its deflection, can be oriented perpendicular to this deflected light beam or to its optical axis, in order to allow the least distorted light exit possible and to form an angle less than 90°, for example, approximately 80° to 89°, preferably approximately 85°, with a prism surface located on the light entry. Thus, for example, the prism surface at the light entry can run exactly vertical, in order to receive a horizontally incoming light beam, and nevertheless the deflection of the light beam according to the invention by less than 90° can then be implemented by this prism.

At the light exit, as a second device for deflection, a deflection prism or deflection mirror can be provided and the second device can be arranged mirror-symmetric to the first device between the entry and exit, so that the optical axis of an angled light beam coming from the reflector runs horizontally on or behind the light exit.

Additional constructions of the invention are the subject matter of claims 9 to 18. This involves, in part, features that are also provided in the device according to DE 10 2004 023 178.8 and that have the advantages described there. Here, the construction according to claim 11 is especially favorable, through which the necessary amount of the sample can be held especially small.

Primarily for the combination of individual or several of the features and measures described above, a device is produced, for which the medium to be examined can be deposited or dropped also in very small and minimal amounts onto an essentially horizontal surface, wherein this receiving position is then preferably crossed twice by the light. This can happen on the way to and from the reflector, wherein a correspondingly large measurement length is produced. Simultaneously, the total overall height of the device is reduced through the skillful light guidance, in which the light beam is directed at an angle to the sample directly after its entry.

Because the medium can be deposited onto an upper receiving location, no special care and no special precautions need to be taken to prevent negative effects due to gravity. Instead, gravity even helps to hold the medium in its position, in which the measurement is to take place. It is sufficient to remove the detachable reflector, to deposit the sample, and to move the reflector back into its position of use, in order to then be able to perform the measurement. Dropping a sample, for example, with the help of a pipette, is a process that can be carried out very easily.

The reflector can be a mirror or a reflective prism and can touch the sample in the position of use with no spacing. The light effectively passes through the sample correspondingly and is deflected back from the reflector, in order to deflect toward the actual detector via the second device for deflection. The measurement path through the sample can be twice as large as the distance of the receiving surface from the surface of the reflector and the light can cover this distance twice, as already explained above.

For a constant accuracy of the measurements and for avoiding changes to the measurement conditions between the individual measurements, as well as relative to reference measurements, it is especially useful when the reflector that can be placed on top or mounted detachably or a cover holding it is locked in rotation and centered relative to the device and its housing in the position of use. In this way it is guaranteed that it is always mounted in the same position relative to the device and its housing and thus also to the receiving position, after a sample was deposited. The appropriate reflection conditions match accordingly.

Here, different structural possibilities are present, which guarantee rotational locking, although the reflector can be removed from its position of use.

So that the reflector obtains the predetermined distance to the receiving position reproducibly in the position of use, this distance can be fixed by at least one spacer between the reflector or cover and housing or by a stop. Thus, for a user there is not the necessity of taking precautions for maintaining the predetermined distance when setting the reflector or the cover with the reflector on the device in its position of use. Also, the construction of the spacer or a stop can be solved structurally in different ways. Here, under certain circumstances, it is even conceivable that the spacer and the holder for the rotational locking of the reflector are combined with each other.

Indeed, the radiation of light onto the device can take place arbitrarily and the detection can also interact with the light exit from the device in a suitable way, wherein arbitrary measurement devices can be used.

It is especially useful, however, when the device has the outer dimensions of an optical cell that can be fitted into a photometer, spectrophotometer, fluorometer, or spectrofluorometer and that can be pumped with light and when the devices for light feeding or light deflection arranged in the interior of the device are arranged in the position of the device, at which for typical optical cells, entry and exit windows for the light used for measurement, wherein the first device for light deflection deflects the light incoming from the photometer to the receiving surface and the second device for light deflection deflects the light coming back from the measurement position to the detector. Through skillful selection of the dimensions of the device according to the invention, this can be inserted into common photometers, spectrophotometers, fluorometers, or spectrofluorometers, in order to also be able to use very small samples of a medium in terms of amount for measurement. This primarily considerably reduces the investment and installation costs.

In this way, the light entry and light exit correspond to those of a conventional optical cell, so that feeding of the light and also its detection after passing through the sample can be performed very easily primarily in corresponding, already existing measurement devices.

For example, the outer dimensions of the cross section of the device can correspond to those of a standard optical cell and can equal, in particular, 12.5 millimeters by 12.5 millimeters.

It should also be mentioned that the light beam coming back out of the device can be aligned with the incoming light beam or can enclose a right angle with this incoming light beam. The latter is useful primarily in fluorometers or spectrofluorometers.

Primarily for the combination of individual or several of the features and measures described above, a device defined above is produced, which allows simple handling and an examination also of very small amounts of a liquid medium independent of its viscosity. Media of relatively high viscosity can also be easily examined, because it can be held without a problem on the essentially horizontal receiving surface. Furthermore, the cleaning after successful measurement is very easy and can be performed, for example, with the help of optical cleaning cloths or with pads. If necessary, typical cleaning means can be used. Here it is preferred that the measurement location charged by the examined medium is very easy to access, wherein the device can even remain in the measurement device.

Overall, a device is produced, which can be used primarily in a construction with optical cell-like dimensions in most commercially available measurement devices and in this way can also be used in older measurement devices without modification. In this way, the device can have an optimized and reduced overall height due to the favorable light guidance, that is, the overall height can have an overall height that is, for example, approximately 5% to approximately 20% or 25% smaller relative to the device shown in DE 10 2004 023 178.8. Reference measurement, sample measurement, and cleaning can be performed easily with less expense and without significant time loss.

BRIEF DESCRIPTION OF THE DRAWINGS

Below, embodiments of the invention are described in more detail with reference to the drawing. Shown, in part, in schematic view.

DETAILED DESCRIPTION OF THE PREFERRED EMBODIMENTS

In the following description, parts of the different embodiments matching in terms of their function receive matching reference numbers even for modified shaping.

Figure 1:
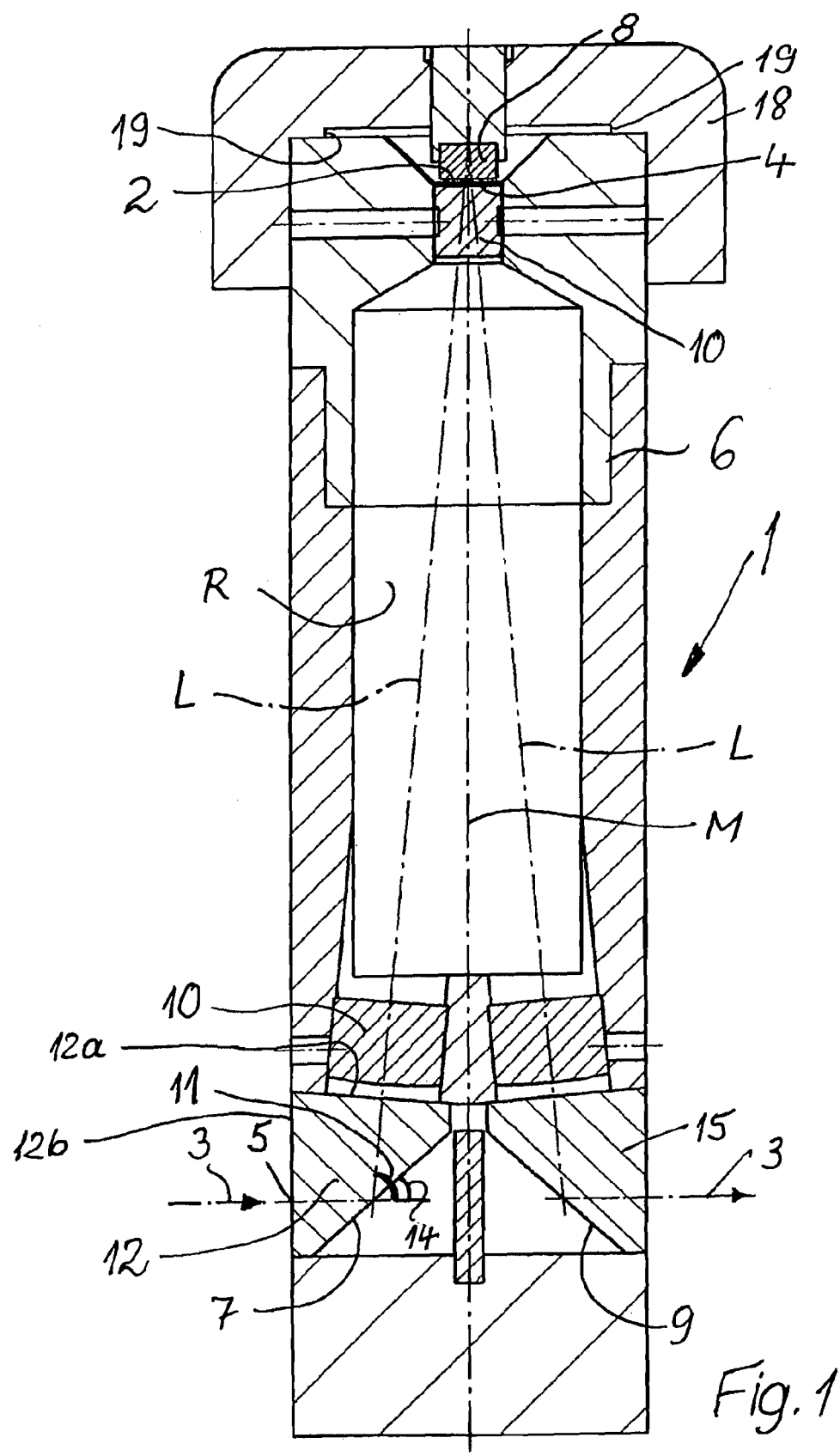
FIG. 1 a longitudinal section view of a device according to the invention with a housing, in which a light beam enters horizontally and is deflected upward at an angle by a first device, wherein an upper planar receiving position is provided for the deposition of the medium to be examined, above which a reflector can be mounted detachably, from which the light reflects back to a second device for further deflecting the light to outside of the device, wherein the light radiates within the housing of the device essentially through a free space, and also FIG. 2 a view corresponding to FIG. 1 for a modified embodiment, in which the light is guided through optical waveguides within the housing of the device over a large part of the height.
Figure 2:
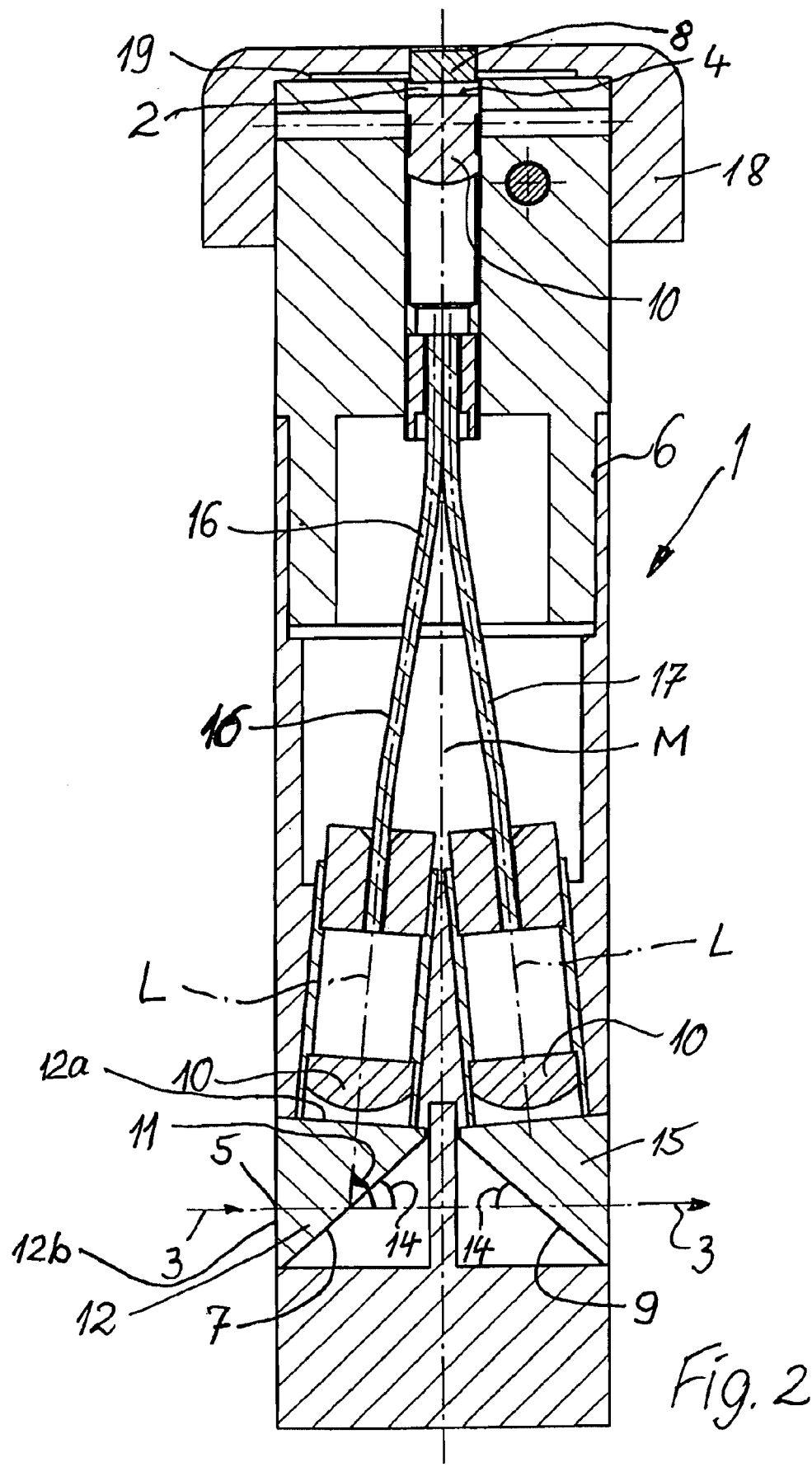

A device designated overall with 1, whose housing 6 and thus also its housing contents are shown in longitudinal section in FIGS. 1 and 2, is used for the analysis or absorption measurement of very small amounts, for example, on a droplet or a fraction of a droplet of a liquid medium 2 with the help of light symbolized by arrows 3, wherein the optical axis of a corresponding light beam is indicated by dash-dot lines L running at an angle to the middle M.

This light is guided through the medium 2 and then detected or analyzed in a known way with a photometer, spectrophotometer, fluorometer, or spectrofluorometer. Here, both embodiments show that the device 1 has an upper planar essentially horizontal and largely flat receiving position 4 for depositing or dropping the medium 2 in the position of use, a horizontally oriented light entry 5 located underneath the receiving position 4 in its housing 6 in the position of use, and a first device 7 located behind the light entry 5 in the beam path for deflecting the light upward to the receiving position 4, and also a reflector 8 that can be mounted detachably above the receiving position 4.

In this way, the reflector 8 has, in the position of use, a defined distance from the receiving position 4, in order to produce a consistently precise measurement path for the light. This distance is filled or can be filled by the medium 2 in the region of the light passage.

Furthermore, the device 1 has a second device 9 for deflecting the light coming from the reflector 8 to a deflector, which is not shown in more detail in FIGS. 1 and 2.

The first device 7 arranged at the light entry 5 for deflecting the light beam in two embodiments is constructed so that the resulting direction of the optical axis—that is, the line L—of the deflected light beam is oriented at an angle upward to the middle of the device 1, wherein the angled position of the optical axis is arranged relative to the device middle M, so that the optical axis of the light beam or light beam bundle is directed without (FIG. 1) or with the help of an optical element (FIG. 2) toward the position of the reflector 8, through which, for example, the longitudinal middle M of the device 1 extends between the light entry 5 and the light exit. The light is deflected practically on the shortest path to the receiving position 4 and the sample, whether it is led through free space within the housing 6 or through an optical element, which can be, according to FIG. 2, an optical waveguide 16.

Here, one recognizes in both figures that before and after the entry of the deflected light beam into the free space (FIG. 1) traversed by it or into an optical waveguide 9, an optical element is provided as a window and/or for bundling the light beam, for example, a convex lens 10. In this way, the light beam can be better bundled and directed more precisely onto the sample. In both embodiments, the optical axis of the light beam 3 runs horizontally before and at the light entry 5 into the housing 6 and the first device 7 for deflecting the light beam deflects its optical axis L by less than 90°, for example, by approximately 85° upward. This deflection angle is indicated with the reference number 11 in the figures. Here, in the region of the light entry 5, as a first device 7 for deflection, a deflection prism 12 or optionally also a deflection mirror is provided, wherein each reflective surface 7 has an angle 14 less than 45° relative to the optical axis of the incident light beam. The deviation of this angle 14 from 45° is half as large as the deviation of the angle 11 from 90°.

On the prism 12 is the surface 12a, through which the light beam exits after deflection upward at an angle, oriented at a right angle to the optical axis L of this deflected light beam, as is easy to see in both figures. Because the prism surface 12b located on the light entry is arranged perpendicular to the incoming light beam 3 and thus exactly vertical, an angle less than 90°, whose magnitude here corresponds to that of the angle 11, is produced between the prism surface 12a and this prism surface 12b on the light entry 5.

At the light exit there is, in turn, as a second device 9 for deflecting the light beam coming from the sample and running at an angle symmetric to the middle M, a deflection prism 15—or optionally a deflection mirror, wherein this second device 9 is arranged mirror-symmetric to the middle M of the device 1 between the entry and exit, so that the optical axis L of a light beam emerging from the reflector 8 and running at an angle to this second device 9 runs horizontally again at or behind the light exit, as can be seen in both figures. The optical axis of the deflected light beam thus runs after the deflection on the shortest possible path to the receiving position 4 or the sample located there and the reflector 8 arranged above, so that a correspondingly small overall height of the device 1 is enabled.

In both embodiments, it is provided that the receiving position 4 is constructed as a surface and is accessible from above. The medium 2 to be examined is held by gravity at this receiving position. Here, the receiving position 4 is dimensioned so large that the light running through to the reflector 8 and reflected back from this reflector passes twice through the receiving position 4 and through the medium. In this way, the measurement path through the sample formed by the medium 2 is twice as large as the distance of the receiving surface 4 from the surface of the reflector 8 and the light covers this distance twice. In this way, the measurement path is twice as large as the mentioned distance.

In the embodiment according to FIG. 1, the light runs from the first device 7 after its deflection practically unhindered through an open space R within the housing 6 to the sample 2 and after reflection from the reflector 8 in the same way back to the second device 9.

In the embodiment according to FIG. 2, however, the light bundle is guided by the optical waveguides 16 and 17 and is therefore compacted in its cross section. Directly after the deflection and before the receiving position 4, however, there is the already mentioned convex lens 10 bundling the light or a corresponding optical window, wherein such a convex lens 10 is then also provided in the reflected light in front of the second device 9.

The receiving position 4 is lowered in both embodiments relative to the upper end side of the housing 6 covered by the reflector 8 or a cover 18 holding this reflector, so that the boundaries of this lowered section simultaneously limit the receiving position 4 and therefore contribute to the fact that a very small amount of a sample is already held and can be examined.

The reflector 8 can be a mirror or a reflective prism and can contact the sample of the medium 2 with no spacing in the position of use. As mentioned, the measurement path through the sample is then twice as large as the distance of the receiving position 4 from the surface of the reflector 8 and the light covers this distance twice for forming the total measurement path.

The reflector 8 that can be placed on top or mounted detachably or the cover 18 holding this reflector according to FIGS. 1 and 2 is locked in rotation and centered relative to the device 1 and its housing 6 in the position of use. The distance of the reflector 8 from the receiving position 4 is here fixed by the spacer 19 between the reflector 8 and housing 6 or—in both embodiments—between the cover 18 holding the reflector 8 and the housing 6. Here, this spacer 19 can preferably rotate like a ring, in order to maintain a uniform distance.

The device 1 preferably has the outer dimensions of an optical cell, which can be fitted into a photometer, a spectrophotometer, fluorometer, or spectrofluorometer and which can be pumped by light, and the devices 7 and 9 arranged in the interior of the device 1 for deflecting light are here arranged at the position, at which for typical optical cells, entry and exit windows are provided for the light used for measurement. The first device 7 for deflecting light deflects the light radiating in from the photometer or the like to the receiving position 4, while the second device 9 is used for deflecting the light coming back from this measurement position to the detector. The outer dimensions of the cross section of the device 1 correspond to those of a standard optical cell and equal, for example, 12.5 mm×12.5 mm.

Therefore, as can be seen in the figures, the optical axis L of the emerging light beam aligns with that of the incoming light beam 3, but these two areas of the light beam could also enclose a right angle if the two devices 7 and 9 are rotated relative to each other accordingly.

The device 1 for the analysis or absorption measurement of a small amount, for example, of a drop or a droplet of a liquid medium 2 with the help of light 3 has an upper planar receiving position 4 for depositing or dropping the medium 2 and a light entry 5 located in the position of use underneath this receiving position or receiving surface 4 in the housing 6 and also, in the beam path behind this light entry 5, a first device 7 for deflecting the light upward to the receiving position 4, where a reflector 8 that can be mounted detachably is also located. Here, the device 7 for deflecting the light beam is constructed so that the direction of the optical axis of the deflected light beam is oriented upward and toward the middle M of the device 1 and the inclined position of the optical axis of the light beam is arranged relative to the device middle M so that it is directed toward the position of the reflector 8, through which the longitudinal middle M runs between the light entry 5 and the light exit of the device 1. The overall height of the device 1 can be correspondingly smaller than one, in which the light is first deflected by a right angle and only then is directed via another change in direction toward the receiving position or sample.

The invention claimed is:

1. Device (1) for the analysis or absorption measurement of a small amount of a liquid medium (2) with the help of light (3), which is guided through the medium (2) and then can be detected or analyzed with a photometer, spectrophotometer, fluorometer, or spectrofluorometer, the device (1) comprising an upper planar receiving position (4) for deposition or dropping of the medium (2) in a position of use, a light entry (5) located in the position of use underneath the receiving position (4) in a housing (6) and a first device (7) located in the beam path at the light entry (5) for deflecting the light upward toward the receiving position (4) and a reflector (8) that is mounted detachably above the receiving position (4) and that has, in a position of use, a defined spacing from the receiving position (4) that is filled or can be filled at least in a region of the light passage by the medium (2), wherein there is a second device (9) for deflecting the light coming from the reflector (8) toward a detector, the first device (7) arranged at the light entry (5) is constructed for deflecting the light beam, so that a resulting direction of an optical axis of the deflected light beam is oriented upward and at an angle to a middle (M) of the device (1) and the angled position of the optical axis is here arranged relative to the device middle (M) so that the optical axis of the light beam is directed without or with the help of at least one optical element toward a position of the reflector (8), through which the longitudinal middle (M) extends between the light entry (5) and the light exit of the device (1).

2. Device according to claim 1, wherein as the optical element for deflecting light beam toward the reflector (8) and then from the reflector (8) to the light exit or to a second device located at the light exit for deflecting the light beam, there is at least one of one lens, one prism or one optical waveguide (16; 17).

3. Device according to claim 1, wherein the light beam runs out from the deflection device unguided or undirected toward the receiving position (4).

4. Device according to claim 1, wherein at least one of before or after the entry of the deflected light beam into the free space (R) traversed by the light beam or an optical waveguide (9) there is an optical element acting as at least one of a window or for bundling the light beam.

5. Device according to claim 1, wherein the optical axis of the light beam (3) extends horizontally at least one of in front of or at the light entry (5) in the housing (6) and the first device (7) for deflecting the light beam deflects its optical axis (L) upward by less than 90°.

6. Device according to claim 1, wherein in a region of the light entry (5), as the first device (7) for deflection, there is a deflection prism (12) or a deflection mirror, having a reflective surface (13) that has an angle (14) less than 45° relative to the optical axis of the incident light beam.

7. Device according to claim 6, wherein on the prism (12), there is a surface (12a), through which the light beam exits after the deflection, that is oriented perpendicular to the deflected light beam or to an optical axis (L) thereof and forms an angle less than 90° with a prism surface (12b) located at the light entry (5).

8. Device according to claim 6, wherein on the light exit, the second deflection device (9) comprises a deflection prism (15) or deflection mirror, and the second deflection device (9) is arranged mirror-symmetric to the middle (M) of the device (1) between the entry and exit, so that the optical axis (L) of a light beam emerging from the reflector (8) and extending at an angle extends horizontally at or behind the light exit.

9. Device according to claim 1, wherein the receiving position (4) is accessible from above and the medium to be examined can be fixed or is held by gravity on the receiving position (4).

10. Device according to wherein the receiving position (4) is dimensioned so large that the light (3) running to the reflector (8) and reflected back from the reflector is guided at least once through the receiving position (4) and through the medium (2).

11. Device according to claim 1, wherein the receiving position (4) has a lowered section relative to an upper end side of the housing (6) covered by the reflector (8) or a cover (18) and boundaries of the lowered section limit the receiving position (4).

12. Device according to claim 1, wherein the reflector (8) is a mirror or a reflective prism and contacts the sample of the medium (2) without spacing in the position of use.

13. Device according to claim 1, wherein the measurement path through the sample is twice as large as a distance of the receiving position (4) from a surface of the reflector (8) and the light covers this distance twice for forming a total measurement path.

14. Device according to claim 1, wherein the reflector (8) can be placed or mounted detachably or a cover (18) holding the reflector is locked in rotation and centered relative to the device (1) and the housing (6) thereof in the position of use.

15. Device according to claim 1, wherein a distance of the reflector (8) from the receiving position (4) is fixed by at least one spacer (19), which is arranged between the reflector (8) or cover (18) and housing (6), or by at least one stop.

16. Device according to claim 1, wherein the device (1) has outer dimensions corresponding to an optical cell, which can be fitted into a photometer, spectrophotometer, fluorometer, or spectrofluorometer and which can be pumped by light, and the devices (7, 9) arranged in an interior of the device (1) for guiding or deflecting light are arranged at a position of the device (1), at which, for typical optical cells, entry and exit windows for the light (3) used for the measurement are provided, wherein the first deflection device (7) deflects the light radiating in from the photometer or the like to the receiving surface (4) and the second device (9) for light deflection deflects the light coming back from the measurement position to a detector.

17. Device according to claim 16, wherein the outer dimensions of a cross section of the device (1) correspond to those of a standard optical cell and equal, in particular, 12.5 mm×12.5 mm.

18. Device according to claim 16, wherein the optical axis (2) of the emerging light beam (3) aligns with that of the incoming light beam or encloses a right angle.

* * * * *